United States Patent [19]

Balaban et al.

[11] Patent Number: 5,209,746
[45] Date of Patent: May 11, 1993

[54] OSMOTICALLY DRIVEN DELIVERY DEVICES WITH PULSATILE EFFECT

[75] Inventors: Stephen M. Balaban, Chesterfield; James B. Pike, St. Peters; Jonathan P. Smith, St. Louis; Clifton A. Baile, Chesterfield, all of Mo.

[73] Assignee: ALZA Corporation, Palo Alto, Calif.

[21] Appl. No.: 837,183

[22] Filed: Feb. 18, 1992

[51] Int. Cl.⁵ .............................................. A61K 9/22
[52] U.S. Cl. .............................. 604/892.1; 604/131; 604/135; 604/890.1
[58] Field of Search ........................ 604/890.1–892.1, 604/93, 131, 135

[56] References Cited

U.S. PATENT DOCUMENTS

| | | | |
|---|---|---|---|
| 3,760,806 | 9/1973 | Leeper | 604/892.1 |
| 4,416,659 | 11/1983 | Simpson et al. | 604/48 |
| 4,507,115 | 3/1985 | Kambarra et al. | 604/891.1 |
| 4,642,230 | 2/1987 | Whitehead et al. | 604/890.1 |
| 4,723,958 | 2/1988 | Pope et al. | 604/890.1 |
| 4,777,049 | 10/1988 | Magruder et al. | 424/457 |
| 4,842,867 | 6/1989 | Ayer et al. | 424/473 |
| 4,867,980 | 9/1989 | Edwards et al. | 424/438 |
| 4,874,388 | 10/1989 | Wong et al. | 604/891.1 |
| 4,957,494 | 9/1990 | Wong et al. | 604/892.1 |
| 4,997,420 | 3/1991 | LeFevre | 604/121 |
| 5,023,088 | 6/1991 | Wong et al. | 424/473 |
| 5,122,128 | 6/1992 | Cordinal et al. | 604/890.1 |

FOREIGN PATENT DOCUMENTS

WO8600519 1/1986 World Int. Prop. O. ....... 604/890.1

Primary Examiner—C. Fred Rosenbaum
Assistant Examiner—Chalin Smith
Attorney, Agent, or Firm—Jacqueline S. Larson; Paul L. Sabatine; Steven F. Stone

[57] ABSTRACT

Osmotically driven delivery capsules which include a beneficial agent and a water absorptive osmotic engine in separate compartments separated by a movable partition are designed to deliver the beneficial agent in a pulsatile manner through an orifice. The pulsatile delivery is achieved by a series of stops along the inner wall of the capsule which obstruct the movement of the partition but which are overcome in succession as the osmotic pressure rises above a threshold level. The number of stops and their placement longitudinally along the length of the capsule establish the number and frequency of the pulses, and the configuration of the partition controls the pulse intensity.

27 Claims, 3 Drawing Sheets

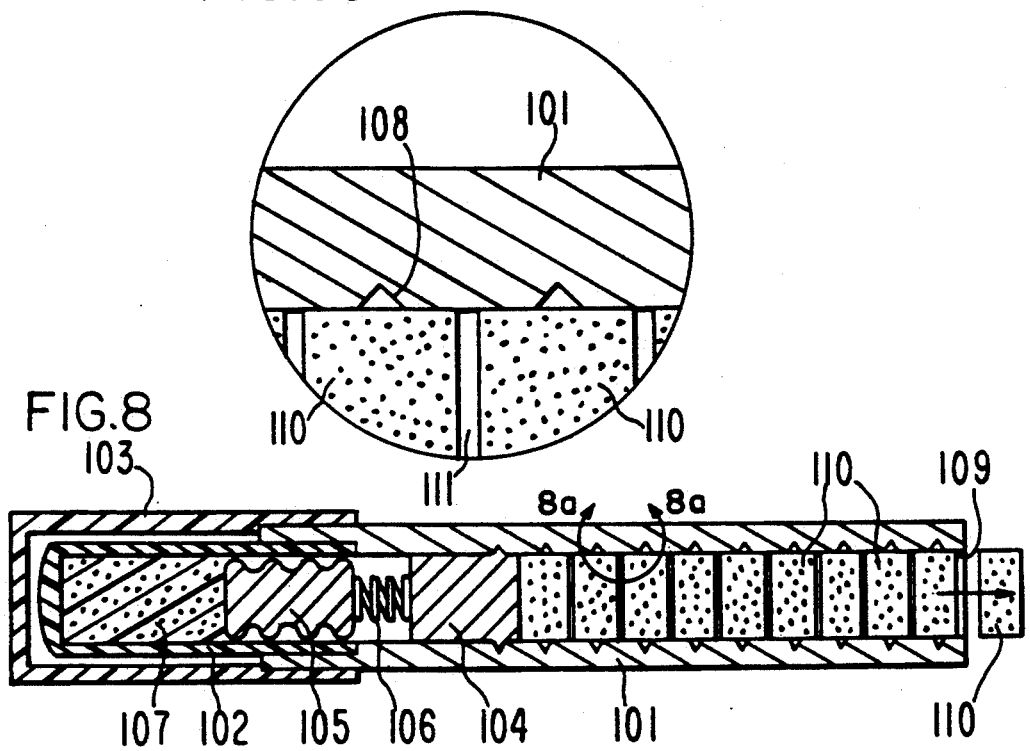
FIG.8a
FIG.8
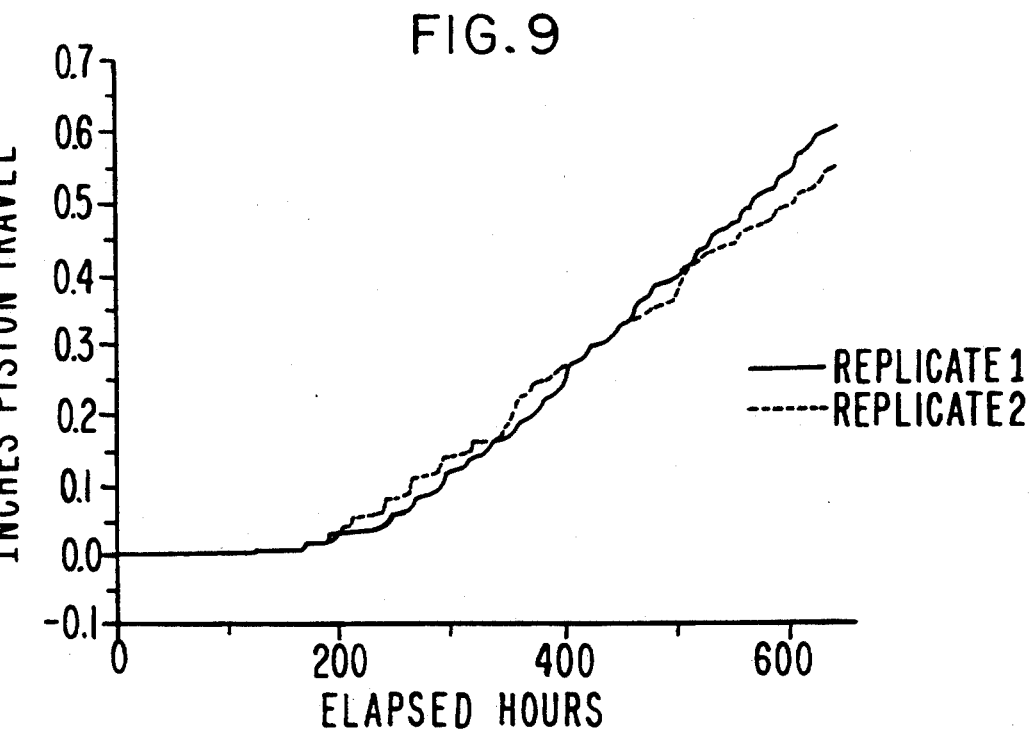
FIG.9

OSMOTICALLY DRIVEN DELIVERY DEVICES WITH PULSATILE EFFECT

This invention lies in the field of controlled- or sustained-release systems for the delivery of drugs, nutrients and the like. In particular, this invention relates to osmotic delivery systems, which are generally in the form of capsules designed to release a beneficial agent through an orifice in the capsule, the release occurring gradually as the result of internal pressure resulting form the imbibition of fluid by the capsule form a surrounding medium.

BACKGROUND OF THE INVENTION

Osmotic delivery capsules, commonly referred to as "osmotic pumps," function by virtue of walls which selectively pass water into the capsule reservoir. Absorption of water by the capsule through these walls is driven by a water-attracting agent in the capsule interior which creates osmotic pressure across the capsule wall. The water-attracting agent may be the beneficial agent itself whose controlled release is sought, but in most cases, it is a separate agent specifically selected for its ability to draw water, this separate agent being isolated from the beneficial agent at one end of the capsule. In either case, the structure of the capsule wall does not permit the capsule to expand, and as a result, the water uptake causes discharge of the beneficial agent through an orifice in the capsule at the same rate that water enters by osmosis.

The terms "osmotically effective" and "osmotically active" are used in the literature to characterize the water-attracting agent which drives the osmotic flow. Certain agents of this type are termed "osmagents," which denotes water-soluble compounds to which the capsule wall is not permeable. Osmotically effective agents which are polymeric species are termed "osmopolymers," which term denotes water-swellable polymers. Osmagents and osmopolymers may be used individually in a capsule or they may be present as a mixture of the two. In cases where the osmotically active agent is separated from the beneficial agent by a movable partition or piston, the osmotically active agent and the compartment in which it resides may be referred to as an "osmotic engine."

Many protocols or situations require, or would benefit from, an intermittent or pulsatile release of the beneficial agent from the capsule. This is true of a variety of drugs, medicaments and nutriments, in a range of environments extending from veterinary medicine to human drug administrations, and to hobby situations such as fish tanks. The reasons vary, and may address such needs as mimicking a natural intermittent physiological release, allowing for periods of restoration of certain body functions between administrations, or adhering to preestablished feeding protocols. One of many examples of situations in which intermittent drug administration is desirable is the administration of somatotropin to swine. Administering the drug in this manner may result in an increase in average daily gain by diminishing the suppression of feed intake, which suppression occurs when the drug is administered at a constant rate and remains at a high level in the bloodstream of the animal. In addition, the pulsed release may increase the therapeutic index of some drugs which would allow for a lower total dose in those cases. Another example is the feeding of fish while one is away on vacation. Other examples abound.

Included in the patent literature relating to pulsatile osmotic pumps is U.S. Pat. No. 4,777,049, issued Oct. 11, 1988 to Magruder, P. R., et al. The pulsatile effect in this patent is achieved by the inclusion of a modulating agent with the beneficial agent to be delivered. The modulating agent is selected on the basis of its solubility in the delivery medium relative to the beneficial agent, and the pulsatile effect results from one of the two falling below its saturation point, causing more of the other to go into solution and thereby be released. The number of pulses one may obtain in this manner is limited, however, and it is difficult to achieve periodic pulses. The system of U.S. Pat. No. 4,723,958, issued Feb. 9, 1989 to Pope, D. G., et al. achieves the pulsatile effect by alternating layers of beneficial agent with layers of inert material. As it is being released, however, the beneficial agent emerges at a slow rate. The system of U.S. Pat. No. 4,842,867, issued June 27, 1989 to Ayer, A. D., et al., is also a layered system, and is best intended for a low number of pulses. Layered systems are also disclosed by Wong, P. S. L., et al., U.S. Pat. No. 4,874,388, issued Oct. 27, 1989; Wong, P. S. L., et al., U.S. Pat. No. 4,957,494, issued Sept. 18, 1990; and Wong, P. S. L., et a., U.S. Pat. No. 5,023,088, issued June 11, 1991.

Devices of the types disclosed in these patents are limited both by their physical configuration and their reliance on the chemicals retained inside them for the pulsatile effect. Control over the intensity and spacing of the pulses which these devices can produce is limited, as is the number of pulses which can be delivered by a single device of reasonable dimensions. Reliability and predictability is also a problem in certain cases.

These and other limitations and disadvantages of known pulsatile delivery systems are addressed by the present invention.

Other literature of possible relevance to this invention are Simpson, B. E., et al., U.S. Pat. No. 4,416,659, issued Nov. 22, 1983; Edwards, S., et al., U.S. Pat. No. 4,867,980, issued Sept. 19, 1989; and LeFevre, R. J., et al., U.S. Pat. No. 4,997,420, issued Mar. 5, 1991. These patents disclose the use of coil springs in slow release capsules. The possible relevance of these patents will be evident form the description which follows:

SUMMARY OF THE INVENTION

The present invention resides in an osmotic delivery capsule which produces an intermittent or pulsatile release of the beneficial agent by virtue of the structure of the capsule itself rather than the chemical composition or placement of materials contained in the capsule. The capsule includes a movable partition which separates the beneficial agent from the osmotically active agent and travels the length of the capsule in response to the expansion of the osmotically active agent. Along its path of travel, the partition encounters a series of stops or similar features spaced at intervals along the inner wall of the capsule which obstruct the passage of the partition. Each stop holds the partition immobile until sufficient pressure accumulates in the compartment containing the osmotically active agent to overcome the resistance an force the partition past the stop. The partition then travels to the next stop, where it is again immobilized while the osmotic pressure builds once again. The delivery pulse of the beneficial agent occurs during the forward motion of the partition. The volume of beneficial agent delivered by the pulse is determined by the distance between successive stops, and the number of pulses which a single capsule can deliver is determined by the number of stops spaced along the capsule wall.

Various embodiments of the invention contain additional features to enhance the performance of the delivery device. One such feature is a closure associated with the orifice through which the beneficial agent is released from the capsule. The closure prevents diffusion of body fluids into the orifice while the partition is stationary between pulses. This is particularly useful when the beneficial agent is sensitive to an aqueous environment. A suitable closure is constructed to function in a manner similar to that of a check valve or relief valve, opening only when the partition is in motion, and returning to a closed position when the partition is immobilized by one of the stops. The closure is generally located close to or across the orifice, and is generally arranged and constructed such that it opens when a pressure differential is imposed, such as that which occurs when the partition is in motion.

Another pulse-controlling feature, which may be used independently of or in conjunction with the closure, is one by which the partition is constructed in two parts or members, the first part or member designed to engage the stops along the enclosure wall in the manner described above, and the second part or member located on the far side of the first member relative to the orifice, the two members separated by a compressible means or linkage such as a spring. For convenience, the first member may be termed a "primary piston" and the second member a "secondary piston." Only the secondary piston is in contact with the osmotically active agent, and as the capsule imbibes water, the swelling of the osmotically active agent forces the secondary piston of the partition against the primary piston, which is immobilized by one of the stops. As the two pistons are drawn together, the compressible linkage is gradually compressed and exerts a continuously increasing pressure on the primary piston. When that pressure exceeds the resistance offered by the stop, the linkage forces the primary piston forward and continues to do so until the primary piston is engaged by the next stop.

In the preferred construction of capsules embodying the features of this invention, the capsule wall surrounding the portion of the capsule interior which houses the osmotically active agent prior to expansion of the agent is the only portion of the wall which is constructed of moisture-permeable material, the remainder of the wall being impermeable to all fluids. This provides improved control over the rate at which the beneficial agent is released from the orifice since it provides a more steady rate of moisture imbibition and avoids dilution of the beneficial agent if the beneficial agent itself has moisture-imbibing properties. This also protects beneficial agents that are unstable when exposed to an aqueous environment. In constructions of this type, the functioning of the osmotically active agent is attributable in part to its location on the side of the partition away from the orifice, in conjunction with the fact that only this agent, and not the beneficial agent, is in contact with the moisture-permeable wall. As a result, the selection of the beneficial agent need not be restricted to those species which are not themselves osmotically active, and there is no need to select two agents which differ widely in water-absorptive properties. Nor is there any need to restrict the beneficial agent to those which are stable in aqueous media. Moisture-sensitive beneficial agents, such as certain proteins, peptides and hormones, may thus be delivered without being adversely affected by fluids entering the device.

Further preferred embodiments and their features, and further objects and advantages of the invention, will be apparent from the description which follows.

BRIEF DESCRIPTION OF THE DRAWINGS

FIG. 8 is a side cross-section view of a sixth example of an osmotic delivery device in accordance with this invention.

FIG. 8a is a magnified view of one section of the device, delineated by 8a-8a in FIG. 8.

FIG. 9 is a plot showing the pulsatile motion of the partition element vs. time observed in an osmotic delivery device constructed according to FIGS. 5, 6 and 7.

DETAILED DESCRIPTION OF THE INVENTION AND PREFERRED EMBODIMENTS

While this invention is of broad scope and capable of application to many different types of osmotic delivery capsules and agents to be delivered by such capsules, the basic elements of the invention and their functions are most easily understood by examination of certain specific embodiments.

Figure 1:
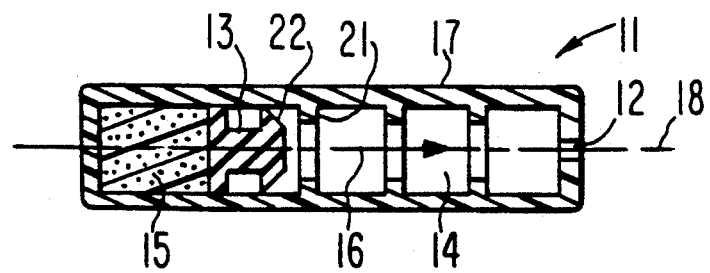
FIG. 1 is a side cross-section view of on example of an osmotic delivery device in accordance with this invention for pulsatile delivery.

FIG. 1 depicts, in cross-section, a capsule which provides a pulsatile effect by intermittently interrupting the delivery with a slow delivery in between the interruptions. The capsule 11 contains an orifice 12 and a partition 13 dividing the capsule interior into a drug reservoir 14 and a compartment 15 (or "osmotic engine") for the osmotically active agent. The partition 13 is a single-piece piston which moves as a unit in the direction indicated by the arrow 16 upon expansion of the osmotically active agent. While the entire shell 17 of the capsule is of a single moisture-permeable material, the osmotically active agent and the drug are selected such that only the osmotic engine 15 undergoes any substantial expansion due to moisture absorption. As a result, the drug is expelled through the orifice 12 only upon movement of the partition 13. Although the drawing is a side cross section view, the capsule shell 17 and the partition 13, when viewed from the end, are both circular. Each is thus a body of revolution about a longitudinal axis 18.

Spaced along the interior of the capsule shell 17 are a series of projections 21 in the form of inwardly extending ribs which encircle the drug reservoir. Three such ribs are shown, equally spaced. The diameter of the partition 13 exceeds the diameter of the opening formed by each projection 21, and as a result, when the outer edge 22 of the forward side of the partition contacts the first projection 21, the partition's advance is halted. With the partition thus immobilized, pressure builds up in the osmotic engine 15 as the osmotically active material in the engine continues to imbibe fluid. Either the partition 13, the capsule shell 17 or both are fabricated from a resilient material, however, and the angled contact surface of the outer edge 22 of the partition causes gradual distortion of either the partition or the projection until sufficient distortion is achieved to permit passage of the partition 13. The partition then resumes its advance in the direction of the arrow 16, driven by the expansion occurring in the osmotic engine, until it contacts the next projection.

The release of the partition 13 from each projection 21 will generally produce a short burst of drug delivery at a high rate followed by a longer delivery at a lower rate, the short burst caused by the release of accumulated pressure in the osmotically active agent. The delivery pattern may be varied however by varying the spacing of the projections and the degree of force required to overcome them.

Figure 2:
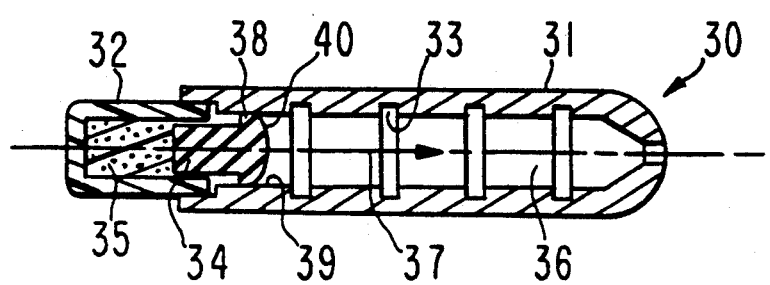
FIG. 2 is a side cross-section view of a second example of such a device.

FIG. 2 depicts a variation on the configuration of FIG. 1. This variation differs in two respects. First, the capsule shell is constructed in two parts, namely a fluid-impermeable tube 31 and a semi-permeable (i.e., moisture-permeable) membrane cup 32. Second, the projections 21 of FIG. 1 are replaced by indentations or grooves 33 which again encircle the drug reservoir.

The partition 34 is initially located at the location at which the fluid-impermeable tube 31 and the membrane cup 32 meet, such that all of the osmotically active agent 35 is contained within the membrane cup prior to expansion, receiving the full benefit of the water absorption while the drug 36 is prevented from being diluted by water absorption. Advance of the pattern occurs in the direction of the arrow 37 as before.

The partition 34 is of a resilient material and has a flared forward end 38 which is larger in diameter than the inner wall 39 of the fluid-impermeable tube. The flared forward end 38 is thus compressed as the partition advances along the capsule, offering resistance to the movement of the partition. When the flared end 38 reaches one of the grooves 33, it expands into the groove as the compression is relaxed. For the partition to resume its forward advance, the flared end 38 must again be compressed. This compression is achieved by increased pressure on the back end of the partition from the osmotic engine, and is facilitated by a rounded edge 40 on the forward face of the flared end 38, which provides the partition with a mushroom shape.

The delivery profile of a capsule such as that depicted in FIG. 2 will be similar to that of FIG. 1, and may be varied in a similar manner.

Figure 3:
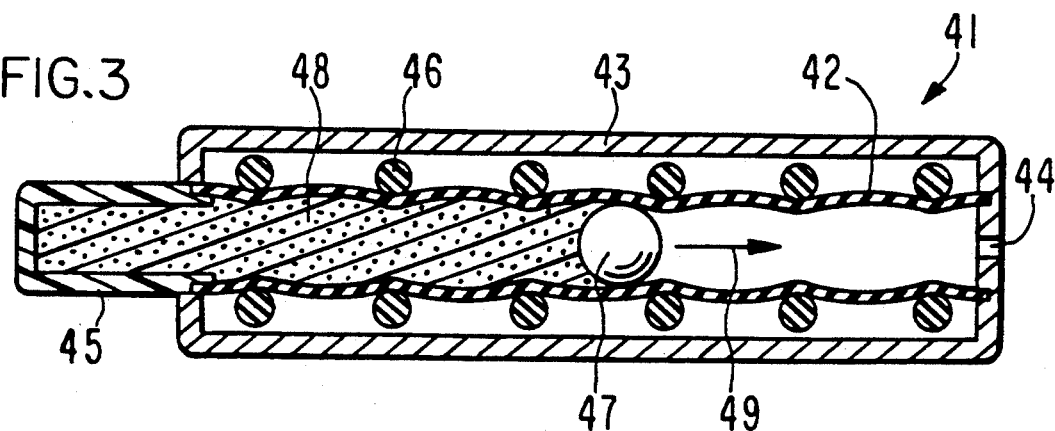
FIG. 3 is a side cross-section view of a third example of such a device.

FIG. 3 illustrates an osmotic delivery capsule in which the stops are formed in a still further manner. The capsule 41 consists of a length of elastomeric tubing 42 inside a housing 43 with an orifice 44 at one end and a semi-permeable membrane cup 45 at the other. Encircling the elastomeric tubing at intervals along its length are a series of constricting rings 46, which may be washers, O-rings, circular springs or the like. Each constricting ring narrows the internal passage in the elastomeric tubing 42 inside the circumference of the ring, presenting an obstruction to the passage of a spherical ball 47 which serves as the movable partition between the drug reservoir and the osmotic engine. The ball 47 upon being driven by the osmotic engine 48, advances in the direction of the arrow 49 until it reaches the narrowed portion formed by one of the rings 46. The ball then comes to rest while the pressure in the osmotic builds to a point where it is sufficient to either expand the ring 46 or compress the wall thickness of the elastomeric tubing 42 sufficiently to permit the ball to pass.

In the capsules of FIGS. 1, 2 and 3, the orifice is an opening with a diameter considerably smaller than that of the beneficial agent reservoir. The purpose is to prevent or at least minimize any backward diffusion of water or other liquids from the capsule surroundings back into the capsule through the orifice. In certain other embodiments of the invention, however, a larger diameter orifice, approaching or equal to that of the reservoir, is preferable. This will be true for example when the beneficial agent is in the form of tablets rather than a liquid, the tablets being equal in diameter to, or of a slightly lesser diameter than, the capsule interior, and packed into the capsule for ejection one at a time. Another example in which a large orifice will be appropriate will be when the osmotic engine of the capsule is submerged in an aqueous environment and the orifice end of the capsule is not, and hence no danger of backward diffusion exists.

Figure 4:
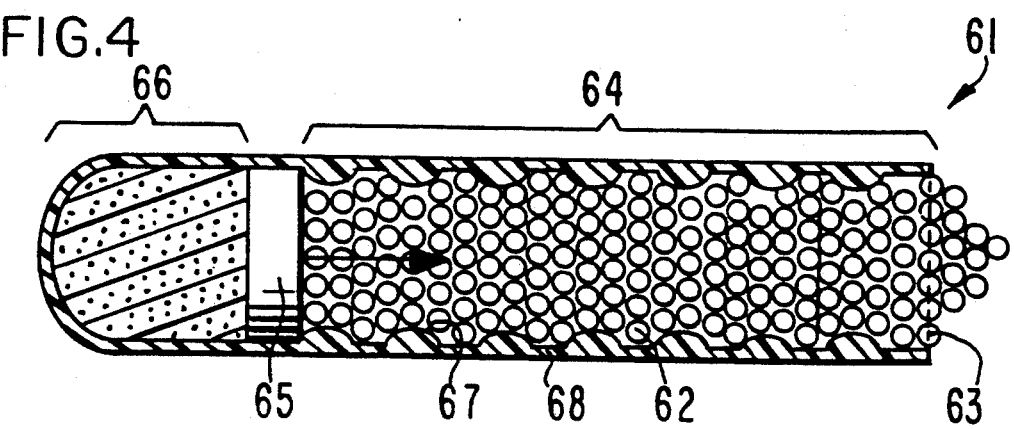
FIG. 4 is a side cross-section view of a fourth example of such a device.

An illustration of the latter is offered by FIG. 4. The delivery device 61 depicted in this drawing is a fish feeder designed to deliver food to a hobbyist's tropical fish in a fish tank while the hobbyist is away from an extended period such as a vacation. The beneficial agent in this device is fish food 62 in particulate form, either spheres as shown or flakes, and the orifice 63 from which the fish food is expelled is the same diameter as the interior of the food reservoir portion 64 of the device.

The device itself is test-tube shaped, with a movable disk-shaped partition 65 inside which separates the osmotically active agent compartment 66 from the food reservoir, and a series of internal ribs 67 periodically spaced along the inner wall of the food reservoir. The portion of the test-tube-shaped shell 68 which surrounds the osmotically active agent compartment (as defined by the initial position of the partition disk 65), and optionally the entire shell, is semi-permeable, permitting water to pass selectively relative to the other materials contained within the device. The partition 65 thus moves from one internal rib 67 to the next by the same mechanism as the partitions of FIGS. 1 and 3, producing intermittent, pulsatile ejection of the food from the orifice.

This device is designed for placement in a fish tank with the orifice 63 above the water level and the osmotically active agent compartment 66 below the water level. Suitable mounting members to support the device in this manner will be readily apparent to those skilled in the art. With the device thus mounted, upward movement of the partition disk 65 will result in the food particles being distributed on the water surface. One advantage of pulsatile surface delivery in this type of application is that all fish are given an equal chance to feed at each pulse. With continuous delivery, more aggressive fish might consume all the food, depriving the remaining fish.

Figure 5:
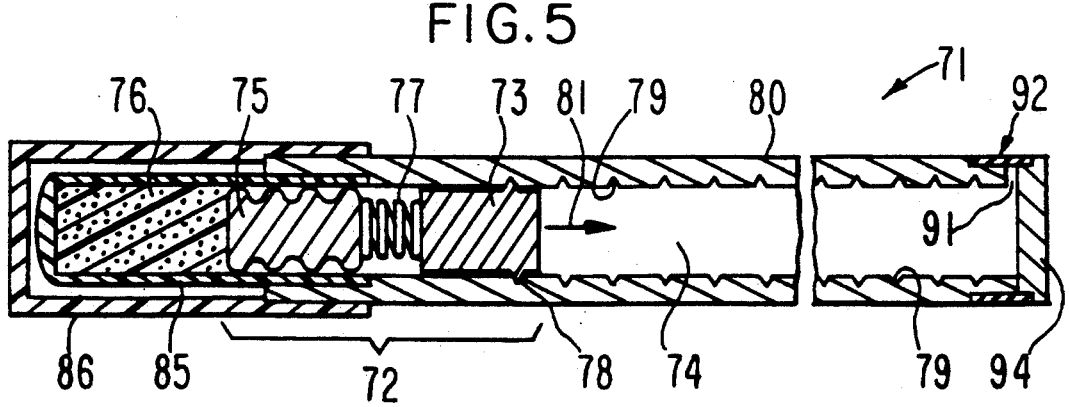
FIG. 5 is a side cross-section view of a fifth example of such a device.

While the partitions shown in FIGS. 1, 2, 3 and 4 are of unitary construction, moving as a unit through the capsule interior, the present invention also extends to more advanced designs such as a composite partition of the type shown in FIG. 5. FIG. 5 depicts a drug delivery capsule 71 which, like those of the preceding drawings is cylindrical in form and symmetrical about its longitudinal axis. The partition 72 of the capsule consists of a primary piston 73 facing the drug reservoir 74 and a secondary piston 75 facing the osmotic engine 76, with a compression coil spring 77 joining the two pistons.

Figure 6:
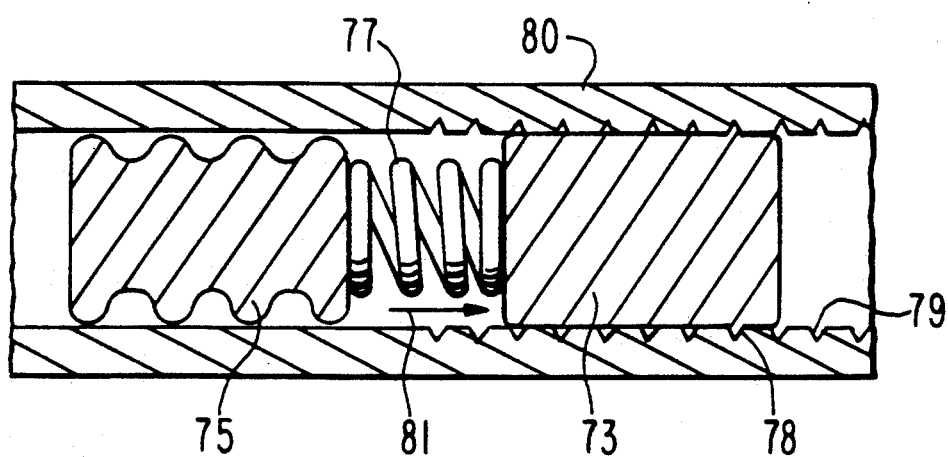
FIG. 6 is an enlarged side cross-section view of the partition element of the device shown in FIG. 5.

The magnified view shown in FIG. 6 shows that the primary piston 73 has a protruding rib 78 around its circumference. This rib engages a series of circular grooves 79 along the inner wall of the capsule shell 80 in succession, in the same manner as the flared forward end 37 and circular grooves 33 of the structure of FIG. 2. The secondary piston 75 does not engage the wall of the capsule shell, but instead is free to move (in the sense that it does not encounter resistance from the wall) in the direction indicated by the arrow 81 in response to expansion of the osmotic engine 76. With continuous imbibition of water by the osmotically active agent in the osmotic engine, the secondary piston 75 advances continuously, compressing the spring 77 until the force exerted by the spring on the primary piston 73 is sufficient to force the protruding rib 78 out of the groove 79 in which it is resting, thereby initiating a delivery pulse. The residual force of the spring then pushes the primary piston further forward until the rib engages the next groove, and the pulse is terminated.

The coil spring 77 shown in FIGS. 5 and 6 may be substituted by any compressible material or linkage which is capable of storing energy upon compression which is later released when the compressive force is removed or overcome. Thus, a compressible gas or an insert of resilient compressible closed-cell foam, or further substitutes which will readily occur to those skilled in the art may be used in place of the spring.

In the composite partition structure shown in FIGS. 5 and 6, the primary piston 73 meets resistance from the capsule wall both during its escapement from a groove 79 and during its transit from one groove to the next due to compression of the protruding rib 78 by the capsule wall. The resistance to escapement from each groove will exceed the resistance to travel between grooves. In preferred embodiments of this aspect of the invention, the ratio of the escapement resistance to the travel resistance will be bout 1.25:1 or higher, and most preferably about 1.5:1 or higher. In preferred embodiments as well, the escapement resistance will require a force differential of about 0.5 pounds force or greater to overcome, most preferably about 1.5 pounds force or greater.

The partition of FIGS. 5 and 6, as well as those of FIGS. 1, 2, and 3, may also be characterized by the pressure differential required to overcome the resistance at each of the grooves, projections or other structural elements which serve as the stops. In preferred embodiments, this threshold pressure differential is at least about 25 psi, most preferably at least about 100 psi.

Further structural and functional parameters of the capsules described above may be varied widely, and appropriate or optimal values and qualities for these parameters will vary with the particular application, such as the nature of the beneficial agent to be delivered, the type of environment into which the delivery is made, and the purpose of and desired protocol for the delivery, including the number, frequency and intensity of the pulses. The design of a system which will produce a selected delivery protocol is well within the routine skill of those experienced in controlled release systems and semi-permeable materials.

As an illustration of some of these parameters, it is noted that the spacing between the stops along the length of the capsule interior and the number of stops may both be varied. The spacing, or linear distances, between stops may be regular or irregular. When irregular, the spacing may be monotonically increasing or decreasing along the direction of travel of the partition, to accommodate variations in the force exerted by the osmotic engine as osmotic absorption progresses, or to accommodate variations in the need for the beneficial agent by the environment as successive pulses are delivered. In preferred embodiments, however, the stops are spaced at equal intervals along the length of the capsule. In either case, the spacing between the stops will in most cases be from about 0.003 inch (0.0076 cm) to about 1.0 inch (2.54 cm), preferably from about 0.01 inch (0.0254 cm) to about 0.3 (0.76 cm). The number of stops is limited only by the length of the capsule. In most cases, capsules in accordance with this invention will contain at least three stops, preferably at least five, and most preferably at least twenty. The length of time between pulses may vary from a few minutes to several weeks, but will generally range from about ten hours to about 100 hours, and in many cases will preferably be about 24 hours to provide beneficial agent on a daily basis.

While these and other structural parameters of capsules in accordance with this invention may vary widely, the following is a list of structural parameters for a representative capsule of the structure shown in FIG. 5:

| | |
|---|---|
| external length of capsule: | 2.0 in (5.08 cm) |
| internal diameter of drug reservoir between grooves: | 0.129 in (0.328 cm) |
| number of grooves: | 42 |
| center-to-center spacing between grooves: | 0.027 in (0.069 cm) |
| depth of each groove: | 0.005 in (0.127 cm) |
| angle of each groove: | 90° |
| primary piston material: | thermoplastic elastomer (Santoprene ®) |
| diameter of primary piston (exclusive of projecting rib): | 0.130 in (0.33 cm) |
| diameter of primary piston at projecting rib: | 0.137 in (0.35 cm) |
| spring material: | stainless steel |
| spring length: | 0.125 in (0.32 cm) |
| spring diameter: | 0.088 in (0.22 cm) |
| spring wire gauge: | 0.012 in (0.03 cm) |
| spring constant: | 12.7 lbf/in (22.2N/cm) |
| spring force at maximum compression: | 0.90 lbf (4.0N) |

FIG. 5 further illustrates a feature related to the construction of the osmotic engine compartment of the capsule, which feature is included in preferred embodiments of the invention. As in FIG. 2, the osmotic engine is retained in a semi-permeable membrane cup 85. The cup is surrounded by a close-fitting sleeve 86 made of rigid material and closed at the end. Both the end wall and the cylindrical side wall of the sleeve 86 have holes (not shown) arranged in a regular pattern to permit access of the surrounding medium to the membrane cup 85. The sleeve 86 prevents the membrane cup from bursting or expanding due to the increasing pressure transmitted by the spring 77 as the result of the osmotic imbibition. The sleeve may be constructed of any inert material capable of withstanding the pressure exerted by the spring at its maximum compression without significant distortion. While the composition of the sleeve may be that of a semi-permeable material, in a presently preferred embodiment, the composition is of a material which is substantially impermeable to fluids (except for the holes). One example is Lexan ® polycarbonate; other examples will be readily apparent to those skilled in the art.

While dimensions and configurations for the sleeve 86 may vary widely, the following is a list representing one example:

| | |
|---|---|
| length of sleeve: | 0.564 in (1.43 cm) |
| wall thickness adjacent to membrane cup: | 0.0375 in (0.095 cm) |
| number of holes in side wall: | 20 |
| diameter of side wall holes: | 0.0625 in (0.159 cm |
| number of holes in end wall: | 3 |
| diameter of end wall holes: | 0.050 in (0.127 cm) |

As in the embodiments discussed above, the beneficial agent is released from the capsule through an orifice 91 at the end of the capsule opposite that of the osmotic engine. While the spring 77 provides each pulse with a sharper profile (as indicated by a plot of quantity of agent released vs. time), the profile may be rendered even sharper by the use of a resilient closure 92 over the orifice. Such a closure will be forced open by the force of the spring 77 when the primary piston 73 is in motion, and will return to a closed position by its own resilient force once the protruding rib 78 of the primary piston (FIG. 6) comes to rest in one of the grooves 79. The closure thus functions as a relief valve or check valve, which not only provides quick opening and closing of the orifice to prevent beneficial agent from seeping or diffusing out between pulses, but also prevents the external medium from diffusing in.

Figure 7:
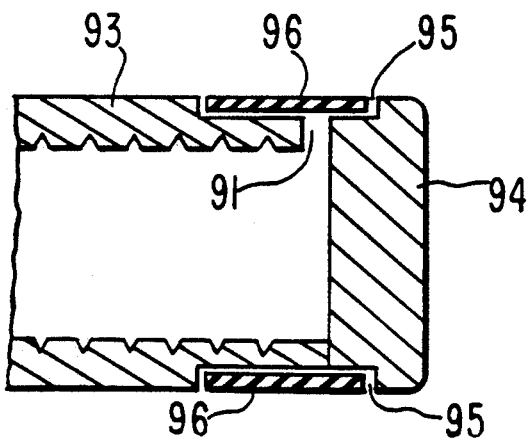
FIG. 7 is an enlarged side cross-section view of the orifice end of the device shown in FIG. 5.

While the orifice and closure may assume a wide variety of structures which will readily occur to those skilled in the art, one example is shown in FIG. 5, and in a magnified view in FIG. 7. The portion of the capsule shell 93 which encloses the drug reservoir 74 is closed at the end 94, and the orifice 91 is a small circular passage through the cylindrical side wall of the shell near the end wall. A rectangular cross-section trough 95 is formed in the outer surface of the cylindrical side wall, encircling the shell, with the orifice 91 located inside the trough. Although only one such orifice is shown, the trough 95 may contain two or more such orifices. A band 96 of resilient material is seated inside the trough, encircling the shell. The band is sufficiently tight to seal the orifice, but capable of being stretched by the force of the primary piston 73 (transmitted through the drug) to separate sufficiently from the orifice to permit escape of the drug. Once the force is spent, the band once again seats against the orifice.

While the materials and dimensions at this end of the capsule may vary widely, the following is a list of parameters of a representative structure:

| | |
|---|---|
| outer diameter of shell: | 0.192 in (0.488 cm) |
| shell wall thickness: | 0.031 in (0.079 cm) |
| trough width: | 0.10 in (0.254 cm) |
| trough depth: | 0.013 in (0.033 cm) |
| orifice diameter: | 0.015 in (0.038 cm) |
| band material: | Santoprene 281-64 |
| outer diameter of band: | 0.162 in (0.41 cm) |
| band width: | 0.10 in (0.254 cm) |
| band thickness: | 0.0185 in (0.047 cm) |

The principles of the present invention may also be used to deliver pelleted beneficial agent in a pulsatile manner, one pellet at a time in spaced intervals. An example of an osmotic delivery capsule for pelleted agents is illustrated in FIG. 8.

This capsule has a construction similar to that of the capsule of FIG. 5, with an identical shell 101, membrane cup 102, sleeve 103, primary piston 104, secondary piston 105, compression coil spring 106, and osmotic engine 107. The primary piston 104 has a protruding rib which mates with circular grooves in the internal wall of the shell 101 in a manner identical to that of the capsule of FIG. 5. The grooves 108 are visible in the magnified view of the capsule wall shown in FIG 8a.

The differences between the capsule and that of FIG. 5 are that this capsule lacks a closure at the delivery end, and has in its place an orifice 109 of the same diameter as the shell itself, and that the beneficial agent is in the form of solid pellets 110 arranged longitudinally along the length of the capsule. The pellets fill the entire interior of the drug reservoir, and will dissolve in the surrounding medium in which the capsule is to be placed. The pellets are separated from each other by a layer 111 of a material which is impermeable by the surrounding medium, however, Thus, in an aqueous environment, the intervening material may be beeswax or any other material which is impermeable by, and insoluble in, water. The intervening material protects the pellet closest to the orifice 109 from contact with bodily fluids until that pellet is discharged from the capsule.

The primary and secondary pistons 104, 105 function in the same manner as in FIG. 5. The combination of the thickness of each pellet 110 and the thickness of one adjacent intervening layer 111 is equal to the spacing between the center of each groove 108. With each advance of the primary piston, therefore, exactly one pellet is discharged from the orifice and the next pellet remains protected by the intervening fluid-impermeable layer.

The materials of construction of this capsule and all other capsules in accordance with this invention are not critical and may vary widely, provided that they are inert, capable of maintaining structural integrity and withstanding the stresses encountered during placement of the capsule and its operation in absorbing moisture. and delivering the beneficial agent, and either semipermeable or impermeable, depending on the portion of the capsule or capsule wall in which they are used. Preferred moisture-permeable wall materials are cellulosic materials, such as cellulose esters, cellulose ethers and cellulose ester-ethers. Those having a degree of substitution ("D.S."), or average number of substitutions per anhydroglucose unit at hydroxyl group positions, ranging from greater than zero up to and including 3.0, are preferred. Examples are cellulose acylate, cellulose diacylate, cellulose triacylate, cellulose acetate, cellulose diacetate, cellulose triacetate, mono-, di-, and tricellulose alkanylates, and mono-, di-, and tricellulose aroylates. Examples expressed in terms of D.S. ranges are cellulose acetate having a D.S. of 1.0 or less and an acetyl content of 21% or less, cellulose acetate having a D.S. of 1.0 to 2.0 and an acetyl content of 21% to 35%, and cellulose acetate having a D.S. of 2.0 to 3.0 and an acetyl content of 35% to 44.8%. Further examples are cellulose propionate with D.S. of 1.8, a propionyl content of 39.2% to 45%, and a hydroxyl content of 2.8% to 5.4%; cellulose acetate butyrate with D.S. of 1.8, and acetyl content of 13% to 15%, and a butyryl content of 34% to 39%; cellulose acetate butyrate with acetyl content of 17% to 53%, a butyryl content of 17% to 53%, and a hydroxyl content of 0.55 to 4.7%; cellulose acetate butyrate with D.S. of 1.8, and acetyl content of 4% and a butyryl content of 51%; cellulose triacylates with D.S. of 2.9 to 3, such as cellulose trivalerate, cellulose trilaurate, cellulose tripalmitate, cellulose trisuccinate, cellulose trioctanoate; cellulose diacylates with D.S. of 2.2 to 2.6, such as cellulose disuccinate, cellulose dipalmitate, cellulose dioctanoate, and cellulose dipentanoate; and coesters of cellulose such as cellulose acetate butyrate and cellulose acetate propionate.

The moisture permeability of the wall surrounding the osmotic engine may be further controlled by the inclusion of modifiers in the wall composition. Modifiers may be selected either to increase or to increase the moisture permeability. Examples of modifiers which decrease the permeability are polycarylate, polymethacrylate, polysulfone, polyacrylic ester, polyacrylonitrile, polyacrylamide, polystyrene, polycaprolactam, polyhexamethylene adipamide, polyhexamethylene sebacamide, polyepoxide, and polyformaldehyde. Examples of modifiers which increase the permeability are polyvinyl alcohol; poly(1,4-anhydro-$\beta$-D-mannuronic acid); polyesters derived from the condensation of a polyhydric alcohol and a polyfunctional acid whose functional groups are hydroxyl groups, carboxyl groups and the like; polysaccharides, hydroxyalkylcelluloses having molecular weights of 9,000 to 35,000; and polyalkylene glycol. Depending on its need, the modifier may be present in the wall material in an amount ranging from about 5% to about 50% by weight Physical characteristics of the wall such as workability and flexibility, lowering of the second-order phase transition temperature and modification of the elastic modulus, may further be enhanced by the inclusion of a plasticizer. Typical plasticizers extend to both straight-chain and branched-chain plasticizers, cyclic plasticizers, acrylic plasticizers and heterocyclic plasticizers. Examples of classes of suitable plasticizers are phthalate, phosphate, citrate, adipate, tartrate, sebacate, succinate, glycolate, glycerolate, benzoate, myristate and sulfonamide plasticizers, including halogenated species. Particular plasticizers of interest are dialkyl phthalates such as dimethyl phthalate, dipropyl phthalate, di(2-ethylhexyl) phthalate, and diisopropyl phthalate; dicycloalkyl phthalates; diaryl phthalates; alkyl phosphates; trialkyl phosphates such as tributyl phosphate and trioctyl phosphate; aryl phosphates and triaryl phosphates such as triphenyl phosphate and tricresyl phosphate; alkyl and trialkyl citrates such as tributyl citrate and triethyl citrate; citrate esters such as acetyl triethyl citrate; alkyl adipates such as dioctyl adipate, diethyl adipate and di(2-methoxyethyl) adipate; alkyl and dialkyl tartrates such as butyl tartrate and diethyl tartrate; alkyl and dialkyl sebacates such as diethyl sebacate, dipropyl sebacate, and dinonyl sebacate; alkyl and dialkyl succinates such as diethyl succinate and dimethyl succinate; alkyl glycolates; alkyl glycerolates; glycol esters and glycerol esters such as glycerol diacetate, glycerol triacetate, glycerol monolactate diacetate and methyl phytyl ethyl glycolate. Plasticizers when included will generally comprise from about 1% to about 45% by weight of the wall composition.

The non-fluid-permeable portion o the capsule wall, the partition separating the osmotic engine from the beneficial agent reservoir, and the close-fitting sleeve surrounding the semi-permeable membrane may be constructed of any material which is inert, fluid impermeable, and of sufficient resilience to function effectively for pulsatile delivery. The need for and degree of resilience will vary depending in part on its location in the capsule, and in part on the capsule structure, as illustrated by the differences among the drawings herein. In general, however, typical materials of construction suitable for these parts include polyolefins, condensation polymers, addition polymers, organo-silicon polymers and inorganic polymers. Specific examples are high density polyethylene, high density polypropylene, polystyrene, polycarbonate, polyamides, elastomers in general, chlorinated rubbers, styrene-butadiene rubbers, chloroprene rubbers, silicones, and glass.

Osmotic delivery capsules in accordance with the present invention for the pulsatile delivery of beneficial agents may be manufactured by a variety of techniques, many of which are described in the literature. In one such technique, the beneficial agent and the osmotically active agent are prepared as solid or semi-solid formulations and pressed into pellets or tablets whose dimensions correspond to the internal dimensions of the respective compartments which they will occupy in the capsule interior. Depending on the nature of the materials used, the two agents and other solid ingredients which may be included with them may be processed prior to the formation of the pellets by such procedures as ballmilling, calendering, stirring or rollmilling to achieve a fine particle size and hence fairly uniform mixtures of each. Once the pellets have been formed, they are placed inside a pre-formed capsule with the partition in between. The capsule may be formed from any of the wall-forming materials disclosed above by the use of a mold, with the materials applied either over the mold or inside the mold, depending on the mold configuration.

In other embodiments of this invention, the beneficial agents are flowable compositions such as liquids, suspension, or slurries, and are poured into the capsule after the osmotically active agent and the partition have been inserted. Still further alternatives may include any of the wide variety of techniques known in the art for forming capsules used in the pharmaceutical industry.

The capsule orifice is also formed by conventional techniques described in the literature. Included among these methods are mechanical drilling, laser drilling, and liquid techniques using an orifice forming agent, such as erosion, extraction, dissolving, bursting or leaching, depending on the nature of the agent used. The capsule will contain at least one such orifice, and in most configurations, one orifice will suffice. The dimensions of the orifice in terms of both diameter and length will vary with the type of beneficial agent and the environment into which it is to be delivered. The considerations involved in determining the optimum dimensions of the orifice for any particular capsule or beneficial agent are the same as those for orifices of capsules of the prior art, and selection of the appropriate dimensions will be readily apparent to those skilled in the art.

Species which fall within the category of osmagent, i.e., the non-volatile species which are soluble in water and create the osmotic gradient driving the osmotic inflow of water, vary widely. Examples are magnesium sulfate, magnesium chloride, potassium sulfate, sodium chloride, sodium sulfate, lithium sulfate, sodium phosphate, potassium phosphate, d-mannitol, sorbitol, inositol, urea, magnesium succinate, tartaric acid, raffinose, and various monosaccharides, oligosaccharides and polysaccharides such as sucrose, glucose, lactose, fructose, and dextran, as well as mixtures of any of these various species.

Species which fall within the category of osmopolymer are hydrophilic polymers that swell upon contact with water, and these vary widely as well. Osmopolymers may be of plant or animal origin, or synthetic. Examples are poly(hydroxy-alkyl methacrylates) with molecular weight of 30,000 to 5,000,000 poly(-vinylpyrrolidone) with molecular weight of 10,000 to 360,000, anionic and cationic hydrogels, polyelectrolyte complexes, poly(vinyl alcohol) having low acetate residual, optionally crosslinked with glyoaxal, formaldehyde or glutaraldehyde and having a degree of polymerization of 200 to 30,000, a mixture of methyl cellulose, crosslinked agar and carboxymethylcellulose, a mixture of hydroxypropyl methylcellulose and sodium carboxymethylcellulose, polymers of N-vinyl lactams, polyoxyethylene-polyoxypropylene gels, polyoxybutylene-polyethylene block copolymer gels, carob gum, polyacrylic gels, polyester gels, polyurea gels, polyether gels, polyamide gels, polyimide gels, polypeptide gels, polyamino acid gels, polycellulosic gels, Carbopol® acidic carboxy polymers having molecular weights of 250,000 to 4,000,000, Cyanamer® polyacrylamides, crosslinked indene-maleic anhydride polymers, Good-Rite® polyacrylic acids having molecular weights of 80,000 to 200,000, Polyox® polyethylene oxide polymers having molecular weights of 100,000 to 5,000,000, starch graft copolymers, and Aqua-Keeps® acrylate polymer polysaccharides.

While the term "drug" appears throughout this specification, its use has been primarily for purposes of convenience. The present invention applies to the administration of beneficial agents in general, which include any physiologically or pharmacologically active substance. Included among the types of agents which meet this description are biocides, sterilization agents, nutrients, vitamins, food supplements, sex sterilants, fertility inhibitors and fertility promoters. Drug agents include drugs which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autocoid systems, the alimentary and excretory systems, the histamine system and the central nervous system. Suitable agents may be selected from, for example, proteins, enzymes, hormones, polynucleotides, nucleoproteins, polysaccharides, glycoproteins, M. lipoproteins, polypeptides, steroids, analgesics, local anesthetics, antibiotic agents, anti-inflammatory corticosteroids, ocular drugs and synthetic analogs of these species.

Examples of drugs which may be delivered by devices according to this invention are prochlorperazine edisylate, ferrous sulfate, aminocaproic acid, mecaxylamine hydrochloride, procainamide hydrochloride, amphetamine sulfate, methamphetamine hydrochloride, benzphetamine hydrochloride, isoproteronol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, theophylline cholinate, cephalexin hydrochloride, diphenidol, meclizine hydrochloride, prochlorperazine maleate, phenoxybenzamine, thiethylperazine maleate, anisindone, diphenadione erythrityl tetranitrate, digoxin, isoflurophate, acetazolamide, methazolamide, bendroflumethiazide, chlorpropamide, tolazamide, chlormadinone acetate, phenaglycodol, allopurinol, aluminum aspirin, methotrexate, acetyl sulfisoxazole, erythromycin, hydrocortisone, hydrocorticosterone acetate, cortisone acetate, dexamethasone and its derivatives such as betamethasone, triamcinolone, methyltestosterone, 17 β-estradiol, ethinyl estradiol, ethinyl estradiol 3-methyl ether, pednisolone, 17 β-hydroxyprogesterone acetate, 19-norprogesterone, norgestrel, norethindrone, norethisterone, norethiederone, progesterone, norgesterone, norethynodrel, aspirin, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, chlorpromazine, methyldopa, dihydroxyphenylalanine, theophylline, calcium gluconate, ketoprofen, ibuprofen, cephalexin, erythromycin, haloperidol, zomepirac, ferrous lactate, vincamine, diazepam, phenoxybenzamine, diltiazem, milrinone, capropril, madol, quanbenz, hydrochlorothiazide, ranitidine, flurbiprofen, fenbufen, fluprofen, tolmetin, alolofenac, mefenamic, flufenamic, difuninal, nimodipine, nitrendipine, nisoldipine, nicardipine, felodipine, lidoflazine, tiapamil, gallopamil, amlodipine, mioflazine, lisinolpril, enalapril, captopril, ramipril, endlapriat, famotidine, nizatidine, sucralfate, etinidine, tetratolol, minoxidil, chlordiazepoxide, diazepam, amitriptylin, and imipramine. Further examples are proteins and peptides which include, but are not limited to, insulin, colchicine, glycagon, thyroid stimulating hormone, parathyroid and pituitary hormones, calcitonin, renin, prolactin, corticotrophin, thyrotropic hormone, follicle stimulating hormone, chorionic gonadotropin; gonadoropin releasing hormone, bovine somatropin, porcine somatotropin, oxytocin, vasopressin, prolactin, somatostatin, lypressin, pancreozymin, luteinizing hormone, LHRH, interferons, interleukins, growth hormones such as human growth hormone, bovine growth hormone and porcine growth hormone, fertility inhibitors such as the protaglandins, fertility promoters, growth factors, and human pancreas hormone releasing factor.

The beneficial agent can be present in this invention in a wide variety of chemical and physical forms, such as solids, liquids and slurries. On the molecular level, the various forms may include uncharged molecules, molecular complexes, and pharmaceutically acceptable acid addition and base addition salts such as hydrochlorides, hydrobormides, sulfate, laurylate, oleate, and salicylate. For acidic compounds, salts of metals, amines or organic cations can be used. Derivatives such as esters, ethers and amides can be used. An active agent can be used alone or mixed with other active agents.

The pulsatile delivery which is provided by devices in accordance with this invention may be for therapeutic purposes, nutritional purposes, preventive purposes, and a wide variety of situations in general. The environments in which the devices may be used include physiological environments within the body of a human or animal, or aqueous environments such as pools, tanks, reservoirs, and the like serving recreational, industrial, or residential purposes. Animals to whom drugs may be administered using systems of this invention include humans and other mammals and warm-blooded animals in general, avians, reptiles and fishes. Household animals, sport animals, farm animals, laboratory animals and zoo animals are included. The invention is of particular interest for application to humans and household, sport and farm animals, particularly mammals. Prominent examples other than humans are sheep, goats, cattle, horses and pigs. For the administration of beneficial agents to animals, the devices of the present invention may be implanted subcutaneously or interperitoneally wherein aqueous body fluids are available to activate the osmotic engine.

The following examples are illustrations of the practice of the invention, and are intended neither to define nor limit the scope of the invention in any manner.

EXAMPLE 1

Preparation of Pulsatile Osmotically Driven Delivery Device

A delivery device of the configuration shown in FIG. 5 is manufactured as follows.

First, an osmotic expandable driving member is prepared by adding 7.6 kg of water and 0.4 kg of polyvinylpyrrolidone to a stainless steel container and mixing the components for 20 hours to obtain a smooth binder solution. Next, 10.0 kg of sodium Carbomer ®, a sodium salt of polyacrylic acid polymer, is sized by being forced through a 0.028 in (0.07 cm) mesh screen in a fluid air mill set at 780–800 rpm speed. Next, 15.0 kg of sodium chloride is sized by being forced through a 0.028 in (0.07 cm) mesh screen in a fluid air mill set at 780–800 rpm speed.

The 10 kg of screened polymer and the 15 kg of screened sodium chloride are transferred to the granulator bowl of a fluid bed granulator, and 6.13 kg of binder solution is slowly sprayed onto the polymer and the salt in the granulator. The polymer/salt granules are formed in this manner. These resultant granules are sized through a 16-mesh screen of a Sweco Separator.

The amount of granulation from the above steps is 25.2 kg, and this is transferred to a blender. Then, magnesium stearate, a lubricant, is added in an amount equal to 1% of the total granulation including the lubricant. A total of 0.255 kg of magnesium stearate is added. All ingredients are mixed for three minutes at 10 rpm to produce a homogeneous expandable driving composition.

The composition thus formed is pressed into osmotically active tablets in a tablet press at a pressure of 500 lb to produce a round, flat-faced 50 mg tablet as an expandable driving member.

The semi-permeable second wall section that forms the compartment for the osmotically active tablet is prepared as follows. First, 3.85 kg of cellulose acetate butyrate and 1.5 kg of tributyl citrate are dry blended in a mixer for 5 minutes. This produces a polymer plasticizer blend of 77/23 ratio for the rate-controlling semipermeable wall. The blend is then placed in an injection mold and molded into a semi-permeable membrane cup of the desired shape with an open end for receiving an expandable driving member and for mating with the forward wall section, whose preparation is as follows.

The forward wall section, which forms the compartment holding the beneficial agent, is prepared by adding 5 kg of polycarbonate (Calibre ® 2000 series, Dow Chemical) to a hopper dryer and drying the polymer at 250° F. for 4 hours. The polymer thus dried is fed into the hopper of an injection mold in which the forward, impermeable, wall section is formed in the desired shape, with an open back end for mating with the semipermeable membrane cup. The forward wall section thus formed is cylindrical, its inside wall having 42 machine triangular grooves along the length of the wall, each groove being 0.005 in (0.013 cm) deep and 0.027 in (0.069 cm) from center to center. The forward wall section also has a circumferential groove on its exterior surface at the anterior end, of rectangular cross section, as shown in FIG. 7. The groove is 0.10 in (0.254 cm) wide and 0.013 in (0.033 cm) deep. In the bottom of this groove, i.e., its cylindrical surface, and centered 0.07 in (0.178 cm) from the posterior side is a 0.015 in (0.038 cm) exit orifice. This orifice is covered by a relief valve band made from medical grade Santoprene ® 281-64, a thermoplastic elastomer, the band having an outer diameter of 0.162 in (0.411 cm), a width of 0.10 in (0.254 cm) and a wall thickness of 0.0185 in (0.047 cm). This band is stretched over the first wall section and seated in the groove, laying flush to the outside wall of the first wall section, thereby filling the annular groove and covering the exit orifice.

The close-fitting sleeve surrounding the semi-permeable membrane cup is prepared by adding 5 kg of polycarbonate (Lexan ® HP 1, General Electric) to a hopper dryer and drying of the polymer at 250° F. for 4 hours. The polymer thus dried is fed into a hopper dryer of an injection molder where a single-cavity hot tip mold is used to injection mold the sleeve in the desired shape, which is 0.564 in (1.43 cm) in length with one open end for mating with the fully assembled delivery device. The internal diameter of the open end is 0.195 in (0.495 cm) and extends 0.164 in (0.417 cm) into the sleeve. At this point, the internal diameter is reduced to 0.160 in (0.406 cm), the outer diameter of the semipermeable membrane cup. Around the smaller diameter portion of the sleeve are formed five sets of holes equally spaced longitudinally on the sleeve, the diameter of the holes being 0.0625 in (0.159 cm). There are also three holes in the closed end of the sleeve, the diameter of these holes being 0.050 in (0.127 cm).

The elastomeric secondary partition or piston is prepared by injection molding Santoprene ® 281-55, a thermoplastic elastomer, into a four-ribbed piston, weighing approximately 31 mg. The piston thus formed is lubricated with silicone medical fluid 1000 cs to facilitate movement of the piston inside the device.

The elastomeric primary piston is prepared in the same manner as the secondary piston. This piston is then fitted with a Buna 25-70 O-ring in one of the end grooves on the piston created by the ribs. This gives the primary piston the dimensions required for it to seat in the triangular grooves in the inner wall of the impermeable forward wall section.

The delivery device is assembled by first charging the subassembly comprising the semi-permeable membrane cup with two of the osmotic tablets. The lubricated secondary piston is then inserted on top of the osmotic tablets, followed by a stainless steel capacitor spring. The spring is 0.125 in (0.32 cm) long, with a diameter of 0.088 in (0.22 cm), a wire gauge of 0.012 in (0.03 cm), a spring constant of 12.7 lbf/in (22.2 N/cm) and a force at maximum compression of 0.90 lbf (4.0N). The primary piston is placed on top of the capacitor spring. Next, the delivery device subassembly comprising the substantially fluid-impermeable forward wall member is filled with 340 mg of beneficial agent formulation at 40° C., wherein the formulation comprised 33.33 weight percent porcine somatotropin, 4.53 weight percent sodium phosphate monobasic, 28.47 weight percent water, 33.0 weight percent glycerol, and 0.67 weight percent Tween ® 80. Then, the two subassemblies are joined at their open ends by partially inserting the membrane cup section into the first wall section. Finally, four drops of moisture-cured cyanoacrylate adhesive are dropped onto the remaining exposed surface, and the members are fully inserted and then twisted to form a sealed delivery device.

The system is completed by joining the sealed delivery device described above with the close-fitting sleeve. These two parts are joined by sliding the sleeve over the membrane cup to seat against the end of the forward wall section on the shoulder inside the sleeve. The sleeve is secured to the first wall section with moisture-cured cyanoacrylic adhesive to effect a sealed, fully protected delivery device.

EXAMPLE 2

Tests For Osmotically Driven Pulsatile Action

Two delivery devices prepared as in Example 1 were tested in vitro, approximating the in vivo conditions in swine.

The device were placed in physiological saline (0.85% salt) at 39° C. The motion of the primary piston in each device was monitored by on-line electronic linear travel gauges interfaced with a PC computer through a converter unit that converts serial signals to RS232 format. Data related to the piston motion was collected continuously in this manner. This data, expressed as the travel of the primary piston vs. time, is presented in FIG. 9. The data demonstrates that, in each of the two delivery devices, the primary piston sat at rest for intervals of approximately 24 hours between forward advances, and that in each forward advance, the primary piston moved a distance of approximately 0.027 in (0.069 cm), which is the distance form one groove to the next in the beneficial agent compartment of the device.

This demonstrates that the primary piston moved in a pulsatile manner in each case, driven solely by the osmotic engine of the device, the pulses governed by the spacing of the grooves.

The foregoing is offered primarily for purposes of illustration. It will be readily apparent to those skilled in the art that the materials, dimensions, manufacturing procedures and other parameters of the system may be further modified or substituted in various ways without departing from the spirit and scope of the invention.

What is claimed is:

1. An osmotically driven device for placement in an aqueous environment for pulsatile delivery of a beneficial agent to said environment, said device comprising:
    an elongate enclosure having a longitudinal axis, first and second ends, an inner wall surface and an orifice at said first end, at least a portion of said enclosure adjacent to said second end being permeable to moisture;
    a partition dividing the interior of said enclosure into first and second compartments adjacent to said first and second ends, respectively, for retention of said beneficial agent and an osmotically active agent, respectively, said partition capable of moving longitudinally within said enclosure;
    a plurality of resistance means on said inner wall surface, said resistance means spaced longitudinally and each preventing movement of said partition toward said first end of said enclosure until a threshold pressure differential across said partition is exceeded.

2. An osmotically driven device in accordance with claim 1 in which each of said resistance means comprises a protrusion on said inner wall surface inhibiting passage of said partition.

3. An osmotically drive device in accordance with claim 1 in which each of said resistance means comprises a protrusion on said inner wall surface, and said partition includes at least one indentation arranged to engage said protrusions in succession.

4. An osmotically driven device in accordance with claim 1 in which each of said resistance means comprises an indentation on said inner wall surface, and said partition includes at least one protrusion arranged to engage said indentations in succession.

5. An osmotically driven device in accordance with claim 1 in which said threshold pressure differential is at least about 25 psi.

6. An osmotically driven device in accordance with claim 1 in which said threshold pressure differential is at least about 100 psi.

7. An osmotically driven device in accordance with claim 1 in which said partition is comprised of first and second members longitudinally arranged in said enclosure and joined to each other by compressible means, said first member positioned closest to said first end of said enclosure and constructed to engage said resistance means, and said second member positioned closest to said second end of said enclosure and constructed to move longitudinally inside said enclosure with substantially less resistance from said enclosure than imposed on said first member.

8. An osmotically driven device in accordance with claim 7 in which said compressible means is comprised of a member selected from the group consisting of a compressible fluid, a closed-cell resilient foam and a spring.

9. An osmotically driven device in accordance with claim 7 in which said compressible means is comprised of a spring.

10. An osmotically driven device in accordance with claim 7 in which each of said resistance means comprises a protrusion on said inner wall surface inhibiting the passage of said first member of said partition.

11. An osmotically driven device in accordance with claim 7 in which each of said resistance means comprises a protrusion on said inner wall surface, and said first member of said partition includes at least one indentation arranged to engage said protrusions in succession.

12. An osmotically driven device in accordance with claim 7 in which each of said resistance means comprises an indentation on said inner wall surface, and said first member of said partition includes at least one protrusion arranged to engage said indentations in succession.

13. An osmotically driven device in accordance with claim 1 further comprising check means inhibiting diffusion of fluid into said enclosure through said orifice.

14. An osmotically driven device for placement in an aqueous environment for pulsatile delivery of a beneficial agent to said environment, said device comprising:
    an elongate enclosure having a longitudinal axis, first and second ends, an inner wall surface and an orifice at said first end, at least a portion of said enclosure adjacent to said second end being permeable to moisture;

a partition dividing the interior of said enclosure into first and second compartments adjacent to said first and second ends, respectively, for retention of said beneficial agent and an osmotically active agent, respectively, said partition comprised of first and second members joined to each other by compressible means, said first member positioned closest to said first end of said enclosure and said second member positioned closest to said second end of said enclosure;

a plurality of stop means on said inner wall surface, spaced longitudinally thereon; said stop means offering a first resistance to passage of said first member, and said inner wall surface between said stop means offering a second resistance to passage of said first member, said second resistance substantially less than said first resistance, and said stop means and said inner wall surface offering substantially less resistance to passage of said second member than to the passage of said first member.

15. An osmotically driven device in accordance with claim 14 in which the ratio of said first resistance to said second resistance is at least about 1.25:1, and said first resistance requires a force differential of at least about 0.5 pounds force to overcome.

16. An osmotically driven device in accordance with claim 14 in which the ratio of said first resistance to said second resistance is at least about 1.5:1, and said first resistance requires a force differential of at least about 1.5 pounds force to overcome.

17. An osmotically driven device in accordance with claim 14 further comprising a closure spanning said orifice, said closure being openable upon the exertion of a pressure differential caused by movement of said first member longitudinally within said enclosure, said closure thereby substantially preventing release of beneficial agent from said enclosure by diffusion or inward diffusion of fluid into said enclosure.

18. An osmotically driven device in accordance with claim 14 in which said compressible means is a member selected from the group consisting of a compressible gas and a spring.

19. An osmotically driven device in accordance with claim 14 in which said compressible means is a coil spring.

20. An osmotically driven device in accordance with claim 1 in which said plurality of resistance means comprises at least three such resistance means spaced longitudinally at substantially equal intervals along said enclosure.

21. An osmotically driven device in accordance with claim 1 in which said plurality of resistance means comprises at least five such resistance means spaced longitudinally at substantially equal intervals along said enclosure.

22. An osmotically driven device in accordance with claim 1 in which said plurality of resistance means comprises at least twenty such resistance means spaced longitudinally at substantially equal intervals along said enclosure.

23. An osmotically driven device in accordance with claim 1 in which said plurality of resistance means are spaced apart by intervals of from about 0.003 inch to about 1.0 inch.

24. An osmotically driven device in accordance with claim 1 in which said plurality of resistance means are spaced apart by intervals of from about 0.01 inch to about 0.3 inch.

25. An osmotically driven device in accordance with claim 1 in which said orifice is substantially equal in cross section to the interior of said enclosure.

26. An osmotically driven device in accordance with claim 1 in which said orifice is substantially smaller in cross section than the interior of said enclosure.

27. An osmotically driven device in accordance with claim 1 in which the movement of said partition toward said first end of said enclosure occurs approximately once every 24 hours.

* * * * *